(12) United States Patent
Lee et al.

(10) Patent No.: US 7,901,923 B2
(45) Date of Patent: *Mar. 8, 2011

(54) **MICROORGANISM OF *ENTEROBACTERIACAE* GENUS HARBORING GENES ASSOCIATED WITH L-CARNITINE BIOSYNTHESIS AND METHOD OF PRODUCING L-CARNITINE USING THE MICROORGANISM**

(75) Inventors: Bheong-Uk Lee, Busan (KR); Whan-Koo Kang, Daejeon (KR); Young-Hoon Park, Seongnam (KR); Eun-Sung Koh, Suwon (KR); Sung-Oh Chung, Seongnam (KR); Jae-Yeong Ju, Seongnam (KR)

(73) Assignee: CJ Cheiljedang Corporation, Seoul (KR)

( * ) Notice: Subject to any disclaimer, the term of this patent is extended or adjusted under 35 U.S.C. 154(b) by 639 days.

This patent is subject to a terminal disclaimer.

(21) Appl. No.: 11/720,008

(22) PCT Filed: Jul. 19, 2005

(86) PCT No.: PCT/KR2005/002323
§ 371 (c)(1),
(2), (4) Date: May 23, 2007

(87) PCT Pub. No.: WO2007/011087
PCT Pub. Date: Jan. 25, 2007

(65) Prior Publication Data
US 2008/0102488 A1      May 1, 2008

(51) Int. Cl.
*C12N 1/12*   (2006.01)
*C12N 9/00*   (2006.01)
*C07H 21/02*  (2006.01)

(52) U.S. Cl. .............. 435/252.1; 536/23.1; 435/183
(58) Field of Classification Search .............. None
See application file for complete search history.

(56) References Cited

U.S. PATENT DOCUMENTS

| | | | |
|---|---|---|---|
| 4,221,869 A | 9/1980 | Vandecasteele et al. |
| 4,371,618 A | 2/1983 | Cavazza |
| 4,708,936 A | 11/1987 | Kulla et al. |
| 5,028,538 A | 7/1991 | Seim et al. |

FOREIGN PATENT DOCUMENTS

| | | |
|---|---|---|
| DE | 3123975 A1 | 3/1982 |
| KR | 1020060005189 A | 1/2006 |
| WO | WO 95/10613 | 4/1995 |
| WO | 2007007987 A1 | 1/2007 |

OTHER PUBLICATIONS

Chung et al., Database WPI Week 200673, Jan. 2006, XP002504316 (Abstract Only).
Galagan et al."The Genome Sequence of Filamentous . . . ", Nature, Apr. 2003, vol. 422, pp. 859-868.
Kaufman, et al., Biosynthesis of carnitine in *Neurospora crassa*, *J. Biol Chem*, Nov. 10, 1977, pp. 7437-7439, vol. 252(21).
Rebouche, et al., Carnitine biosybthesis in *Neurospora carassa*: enzymatic conversion of lysine to epsilon-N-trimethyllysine, *J. Bacteriol*, Jun. 1976, pp. 1207-1214, vol. 126(3).
International Search Report (Form PCT/ISA/210); PCT/KR2005/002323; Mailed Apr. 19, 2006 (5 sheets).

*Primary Examiner* — Alexander D Kim
(74) *Attorney, Agent, or Firm* — Rothwell, Figg, Ernst & Manbeck PC

(57) ABSTRACT

Provided is a microorganism belonging to the family Enterobacteriaceae including: a polynucleotide encoding N-trimethyllysine hydroxylase activity derived from *Neurospora crassa*; a polynucleotide encoding 3-hydroxy-6-N-trimethyllysine aldolase activity derived from *Neurospora crassa*; a polynucleotide encoding γ-trimethylaminoaldehyde dehydrogenase activity derived from *Neurospora crassa*; and a polynucleotide encoding γ-butyrobetaine hydroxylase activity derived from *Neurospora crassa*. Provided is also a process for producing L-carnitine using the microorganism.

7 Claims, 8 Drawing Sheets

US 7,901,923 B2

MICROORGANISM OF ENTEROBACTERIACAE GENUS HARBORING GENES ASSOCIATED WITH L-CARNITINE BIOSYNTHESIS AND METHOD OF PRODUCING L-CARNITINE USING THE MICROORGANISM

CROSS REFERENCE TO RELATED APPLICATION

This application is a 35 U.S.C. §371 National Phase Entry Application from PCT/KR2005/002323, filed Jul. 19, 2005, and designating the United States.

BACKGROUND OF THE INVENTION

1. Field of the Invention

The present invention relates to a microorganism belonging to the family Enterobacteriaceae including L-carnitine biosynthesis-associated genes derived from *Neurospora crassa*, and a process for producing L-carnitine using the same.

2. Description of the Related Art

L-carnitine (3-hydroxy-4-trimethylaminobutyrate), which is commonly present in an organism, is a zwitterionic compound responsible for the transportation of activated long-chain fatty acids into the mitochondrial matrix via the membrane of the mitochondria. It is known that L-carnitine is biosynthesized from lysine or lysine in protein (hereinafter, referred to as "protein lysine"). Mammalian protein lysine is generally used as a precursor for L-carnitine biosynthesis. However, in *Neurospora crassa*, free lysine is used as a precursor of L-carnitine. In the biosynthesis of L-carnitine, ε-N,N,N-trimethyllysine, ε-N,N,N-trimethyl-β-hydroxylysine, N,N-trimethylaminobutyraldehyde, and γ-butyrobetaine are formed as intermediates. γ-butyrobetaine is hydroxylated to L-carnitine by γ-butyrobetaine hydroxylase. FIG. 1 illustrates putative L-carnitine biosynthesis pathway in *Neurospora crassa*.

L-carnitine can be produced by chemical synthesis, enzymatic semisynthesis, or microbiological method. However, the chemical synthesis of carnitine unavoidably leads to DL-carnitine racemic mixtures, and thus requires separation of the DL-racemic mixtures. With respect to the enzymatic semisynthesis of L-carnitine, for example, U.S. Pat. No. 4,221,869 discloses a process for producing L-carnitine from dehydrocarnitine using carnitine dehydrogenase (EC 1.1.1.108) and a coenzyme, NAD. However, dehydrocarnitine is very unstable and thus can be spontaneously decomposed into acetonyltrimethylammonium and carbon dioxide. German Patent No. DE-OS-3123975 discloses a process for producing L-carnitine from γ-butyrobetaine using γ-butyrobetaine hydroxylase (EC 1.14.11.1) isolated from *Neurospora crassa*. However, there is a disadvantage that α-ketoglutarate and a reducing agent (i.e., ascorbate) must be added to the reaction mixture during hydroxylation.

With respect to the production of L-carnitine by microbiological method, U.S. Pat. No. 5,028,538 discloses a process for producing L-carnitine, which includes incubating *E. coli* 044 K 74 in a culture medium containing crotonobetaine (4-N,N,N-triethylaminocrotonic acid) and recovering L-carnitine from the culture. U.S. Pat. No. 4,708,936 discloses a process for producing L-carnitine by incubating *Achromobacter xylosoxydans* DSM 3225 (HK 1331b) in a crotonobetaine- and/or γ-butyrobetaine-containing medium. According to this process, however, the use of crotonobetaine which is neither a precursor nor an intermediate for L-carnitine biosynthesis is required and the yield of L-carnitine is not high. Thus, the microbiological method needs to improve the yield of L-carnitine.

Therefore, while searching for L-carnitine-producing microorganism capable of producing L-carnitine with high yield using an inexpensive precursor, the present inventors found that L-carnitine biosynthesis-associated genes derived from *Neurospora crassa* were well expressed in a microorganism belonging to the family Enterobacteriaceae, and thus completed the present invention.

SUMMARY OF THE INVENTION

The present invention provides a microorganism for producing L-carnitine with high yield.

The present invention also provides a process for producing L-carnitine using the microorganism.

DISCLOSURE OF THE INVENTION

According to an aspect of the present invention, there is provided a microorganism belonging to the family Enterobacteriaceae including: a polynucleotide encoding N-trimethyllysine hydroxylase (TMLH) activity derived from *Neurospora crassa*; a polynucleotide encoding 3-hydroxy-6-N-trimethyllysine aldolase (SHMT) activity derived from *Neurospora crassa*; a polynucleotide encoding γ-trimethylaminoaldehyde dehydrogenase (TMABADH) activity derived from *Neurospora crassa*; and a polynucleotide encoding γ-butyrobetaine hydroxylase (BBH) activity derived from *Neurospora crassa*.

The microorganism of the present invention is not limited provided that it includes the four polynucleotides encoding the respective four proteins. Preferably, the microorganism is *Escherichia coli* (*E. coli*), and more preferably *E. coli* KCCM-10581.

The four polynucleotides encoding the respective four proteins, i.e., TMLH, SHMT, TMABADH, and BBH, can be introduced into microbiological cells via a vector or by themselves. In a case where the four polynucleotides encoding the respective four proteins are introduced into microbiological cells via a vector, the four polynucleotides can be contained in a single vector or in two or more vectors. As used herein, the term "vector" has a meaning well known in the art and generally refers to a nucleic acid construct used for introduction of nucleic acids into cells. Preferably, such a nucleic acid construct is a plasmid or a viral genome-derived nucleic acid construct.

In the present invention, the polynucleotide encoding TMLH activity derived from *Neurospora crassa* encodes TMLH derived from *Neurospora crassa*. It is known that TMLH catalyzes the conversion of ε-N-trimethyllysine to β-hydroxy-ε-N-trimethyllysine in *Neurospora crassa* cells, but the present invention is not limited to such a specific action mechanism of TMLH. Preferably, the polynucleotide encoding TMLH is a polynucleotide encoding an amino acid sequence as set forth in SEQ ID NO: 9, and more preferably, a polynucleotide having a nucleotide sequence as set forth in SEQ ID NO: 13.

The polynucleotide encoding SHMT activity derived from *Neurospora crassa* encodes SHMT derived from *Neurospora crassa*. It is known that SHMT catalyzes the conversion of β-hydroxy-ε-N-trimethyllysine to γ-N-trimethylaminobutyraldehyde in *Neurospora crassa* cells, but the present invention is not limited to such a specific action mechanism of SHMT. Preferably, the polynucleotide encoding SHMT is a polynucleotide encoding an amino acid sequence as set forth in SEQ ID NO: 10, and more preferably, a polynucleotide having a nucleotide sequence as set forth in SEQ ID NO: 14.

The polynucleotide encoding TMABADH activity derived from *Neurospora crassa* encodes TMABADH derived from *Neurospora crassa*. It is known that TMABADH catalyzes the conversion of γ-N-trimethylaminobutyraldehyde to γ-butyrobetaine in *Neurospora crassa* cells, but the present invention is not limited to such a specific action mechanism of TMABADH. Preferably, the polynucleotide encoding TMABADH activity is a polynucleotide encoding an amino acid sequence as set forth in SEQ ID NO: 11, and more preferably, a polynucleotide having a nucleotide sequence as set forth in SEQ ID NO: 15.

The polynucleotide encoding BBH activity derived from *Neurospora crassa* encodes BBH derived from *Neurospora crassa*. It is known that BBH catalyzes the conversion of γ-butyrobetaine to L-carnitine in *Neurospora crassa* cells, but the present invention is not limited to such a specific action mechanism of BBH. Preferably, the polynucleotide encoding BBH activity is a polynucleotide encoding an amino acid sequence as set forth in SEQ ID NO: 12, and more preferably, a polynucleotide having a nucleotide sequence as set forth in SEQ ID NO: 16.

According to another aspect of the present invention, there is provided a process for producing L-carnitine, which includes culturing a microorganism of the present invention in the presence of a substrate selected from the group consisting of ε-N-trimethyllysine, β-hydroxy-N-trimethyllysine, γ-N-trimethylaminobutyraldehyde, γ-butyrobetaine, and a mixture thereof to produce L-carnitine in the culture.

In the process for producing L-carnitine of the present invention, the microorganism of the present invention is as described above.

In the process for producing L-carnitine of the present invention, the concentration of the substrate selected from the group consisting of ε-N-trimethyllysine, β-hydroxy-N-trimethyllysine, γ-N-trimethylaminobutyraldehyde, γ-butyrobetaine, and a mixture thereof is not particularly limited. Preferably, however, the concentration of the substrate ranges from 0.1 to 10 wt % based on the weight of the culture medium.

In the process for producing L-carnitine of the present invention, L-carnitine in the culture can be recovered by separation and purification. The separation and purification are well known in the art. By way of a non-limiting example, the recovery of L-carnitine can be done by separating a supernatant from the cell culture by ultrafiltration, centrifugation, or decantation, followed by cation exchange chromatography or electrodialysis, and then recrystallization.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
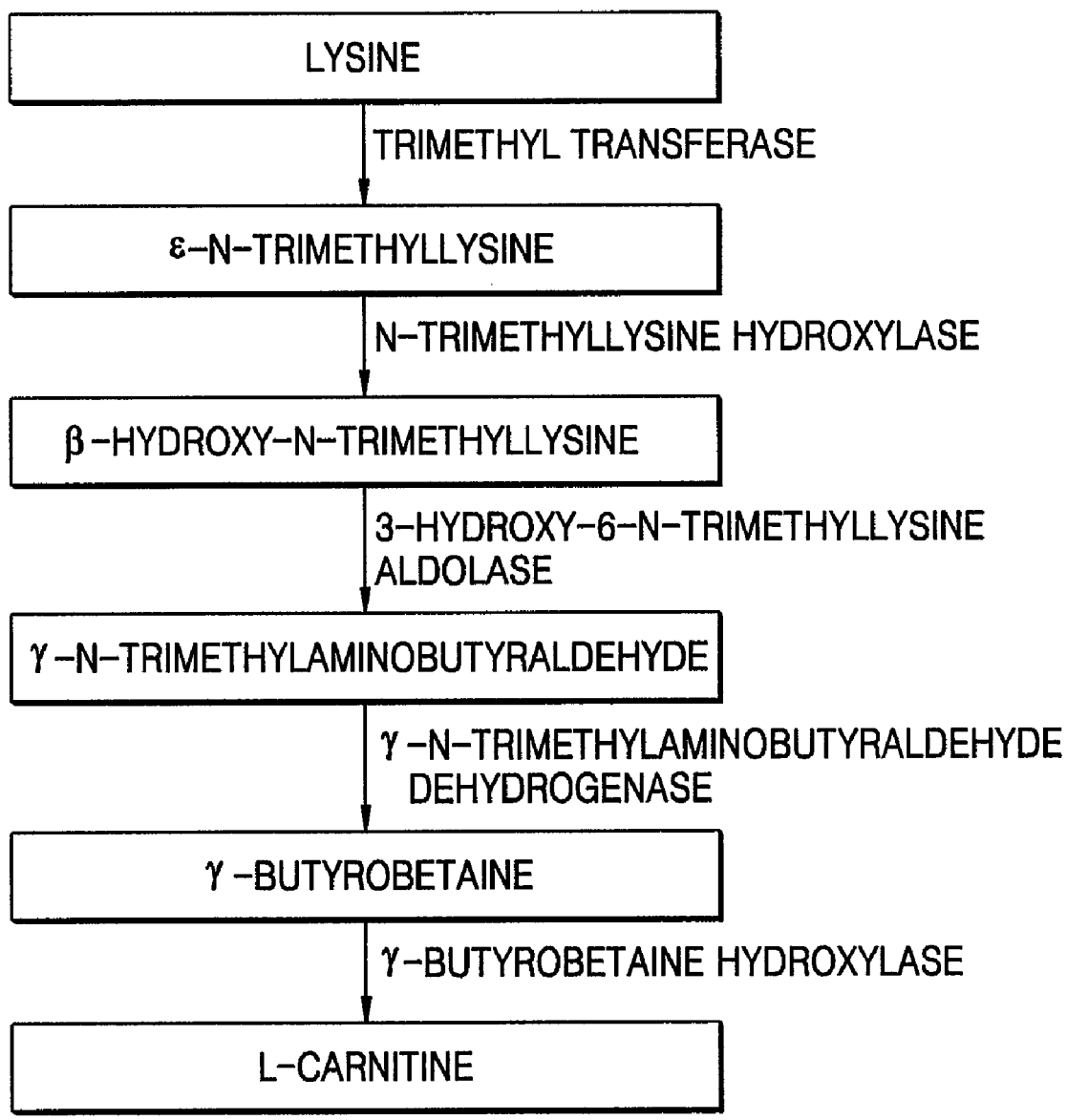
FIG. 1 illustrates a putative L-carnitine biosynthesis pathway in *Neurospora crassa*.

Hereinafter, the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Hereinafter, the present invention will be described more specifically with reference to the following examples. The following examples are for illustrative purposes and are not intended to limit the scope of the invention.

EXAMPLES

In the following Examples, four polynucleotides encoding respective proteins associated with L-carnitine biosynthesis derived from *Neurospora crassa* were selected and nucleic acid constructs including the polynucleotides were constructed. The nucleic acid constructs were transformed into *E. coli* strains. The transformed *E. coli* strains were cultured in media containing L-carnitine biosynthesis intermediates to produce and recover L-carnitine.

Example 1

Separation of Four Polynucleotides, Respectively, Encoding N-trimethyllysine Hydroxylase (TMLH), 3-Hydroxy-6-N-Trimethyllysine Aldolase (SHMT), γ-Trimethylaminoaldehyde Dehydrogenase (TMABADH), and γ-Butyrobetaine Hydroxylase (BBH) from *Neurospora crassa*

In this Example, four polynucleotides encoding respective TMLH, SHMT, TMABADH, and BBH were separated from *Neurospora crassa* and cloned, and the sequence analyses of the cloned polynucleotides were performed.

(1) Preparation of cDNA Library of *Neurospora crassa*

Total mRNAs were separated from a culture containing the fungus thallus (including the sporophyte) of *Neurospora crassa* and reversely transcribed using a poly-T primer. The obtained cDNAs were amplified by PCR, digested with EcoRI and XhoI, and inserted into the EcoRI-XhoI site of a λ AD5 cloning vector, to prepare a *Neurospora crassa*-derived cDNA library.

Next, the cDNA library was transformed into *E. coli* BNN322. The transformed *E. coli* BNN322 was cultured to amplify the cDNA library. For this, first, *E. coli* BNN322 was cultured overnight in an LB medium containing 50 μg/ml of kanamycin and 0.2% of glucose. The obtained culture was centrifuged. A supernatant was removed and a cell pellet was resuspended in 1 ml of 10 mM MgSO4. The obtained suspension and 5×10⁷ PFU of the λ cDNA library were cultured without shaking at 30° C. for 30 minutes. 2 ml of a LB medium was further added to the culture and the resultant culture was cultured with shaking at 30° C. for one hour. The cultured cells were plated onto an ampicillin (75 µg/ml)-containing LB medium plate, and cultured at 37° C. for 8 hours. cDNA library pools were purified from colonies of the plate using Wizard kit. λ phages containing the purified cDNA library pools was used as a template for amplification of four polynucleotides encoding respective TMLH, SHMT, TMABADH, and BBH.

(2) Amplification and Cloning of TMLH-Encoding Polynucleotide (carB Gene) and Detection of TMLH Production (a) Amplification and Cloning of TMLH-Encoding Polynucleotide (carB Gene)

PCR was performed using the cDNA library pool-containing λ phages of (1) as template and oligonucleotides set forth in SEQ ID NOS: 1 and 2 as primers. The PCR products were subjected to agarose gel electrophoresis. As a result, desired PCR products of about 1.4 kb were identified. The primers of SEQ ID NOS: 1 and 2 included putative sequences encoding the start codon and the stop codon of *Neurospora crassa*-derived TMLH. The *Neurospora crassa*-derived TMLH was deduced by homology search between publicly available human- and rat-derived TMLH amino acid sequences and the amino acid sequences of total proteins expressed from *Neurospora crassa* genome, and the primers of SEQ ID NOS: 1 and 2 were designed based on the putative *Neurospora crassa*-derived TMLH.

Figure 2:
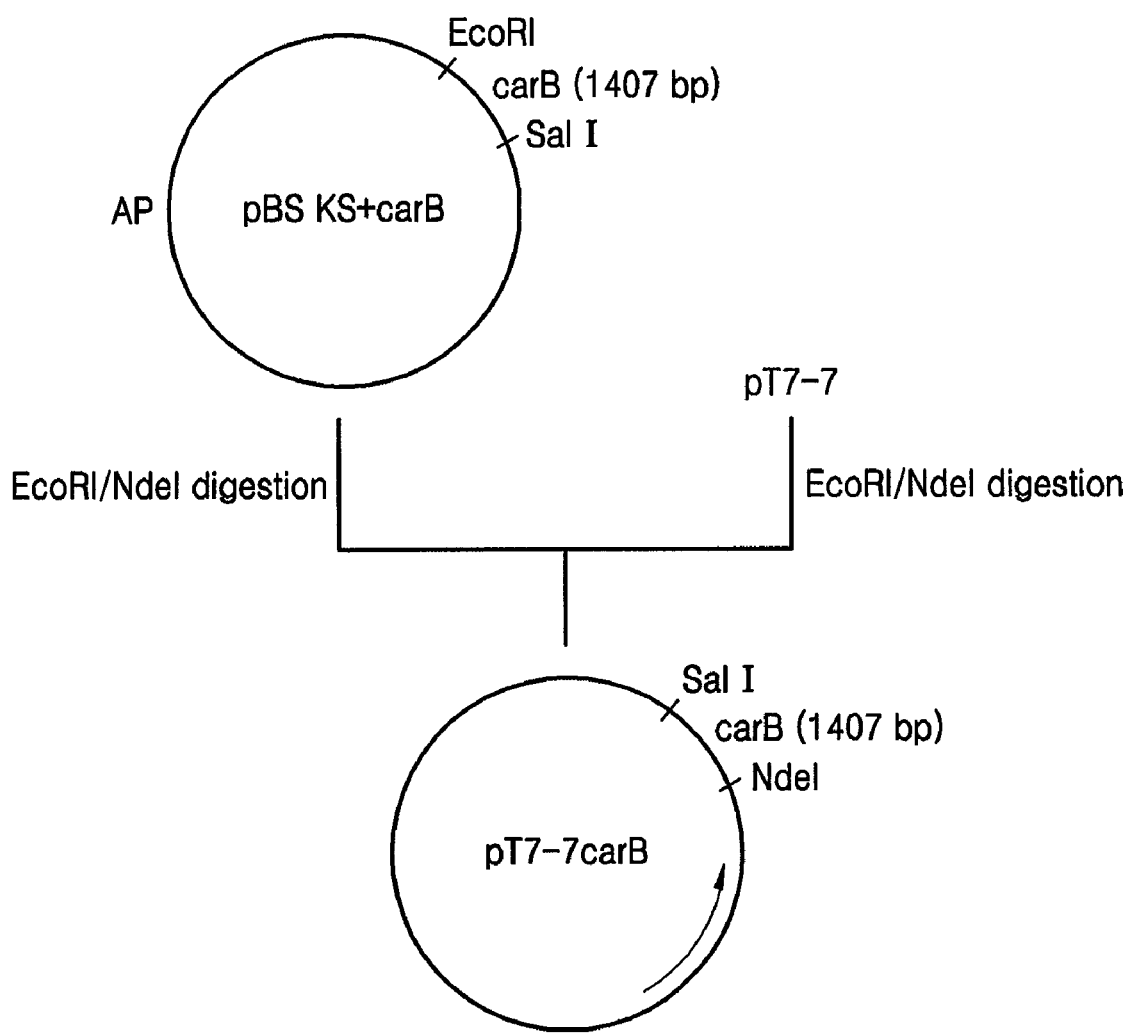
FIG. 2 is a diagram showing the construction of pT7-7carB.

The PCR products were digested with EcoRI and SalI, and ligated into pBS KS+ (Stratagene Inc.) which had been treated with the same restriction enzymes. pBS KS+carB obtained by inserting the PCR products into pBS KS+ was transformed into *E. coli* DH5α. The transformed *E. coli* DH5α was cultured at 37° C. for 8 hours. pBS KS+carB was separated from the transformed *E. coli* DH5α and treated with EcoRI and SalI to determine whether the PCR products were appropriately inserted into *E. coli* DH5α. Then, the separated pBS KS+carB was treated with NdeI and SalI and subjected to agarose gel electrophoresis to obtain NdeI-SalI fragments. The NdeI-SalI fragments were ligated into expression vectors pT7-7 which had been treated with the same restriction enzymes to obtain pT7-7carB (see FIG. 2). The pT7-7carB was transformed into *E. coli* BL21 (DE3).

(b) Detection of TMLH Production

Figure 6:
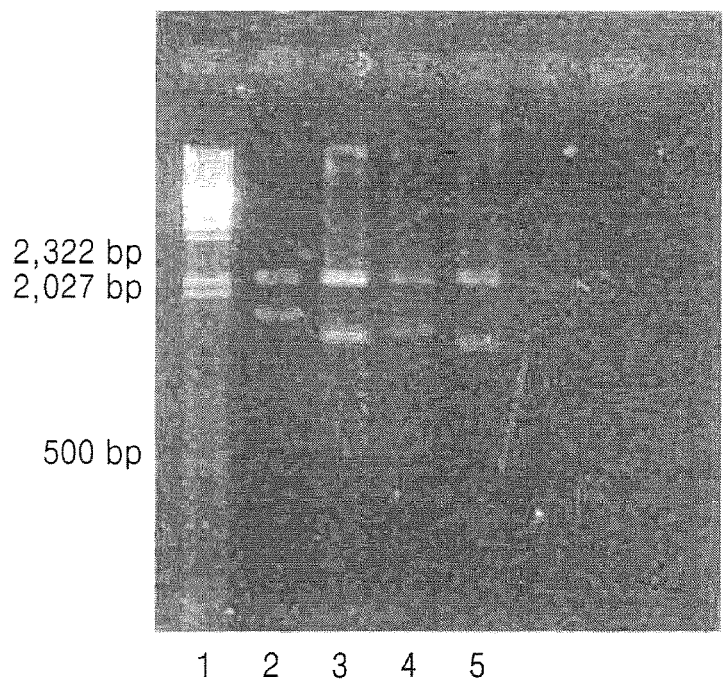
FIG. 6 is an electrophoretic image for genes respectively inserted into pT7-7carB, pT7-7carC, pT7-7carD, and pT7-7carE (lane 1: marker, lane 2: carB, lane 3: carC, lane 4: carD, and lane 5: carE)

The pT7-7carB-transformed *E. coli* BL21(DE3) was cultured at 37° C. in a 250 ml-baffled flask filled with 50 ml of an ampicillin (100 µg/ml)-supplemented LB medium until OD600 was 0.6. 1 mM of IPTG was added and the resultant cells were further cultured for four hours. pT7-7carB was separated from the cell culture and treated with NdeI and SalI, and the resultant restriction fragments were separated using agarose gel electrophoresis. The electrophoretic results are shown in FIG. 6. As shown in FIG. 6, a band corresponding to the NdeI-SalI fragment was observed (lane 2). The nucleotide sequence analysis of the carB in pT7-7carB revealed that the nucleotide sequence of the carB in pT7-7carB was the same as that found in the *Neurospora crassa* genome database of the National Center for Biotechnology Information (NCBI) (SEQ ID NO: 13).

Figure 7:
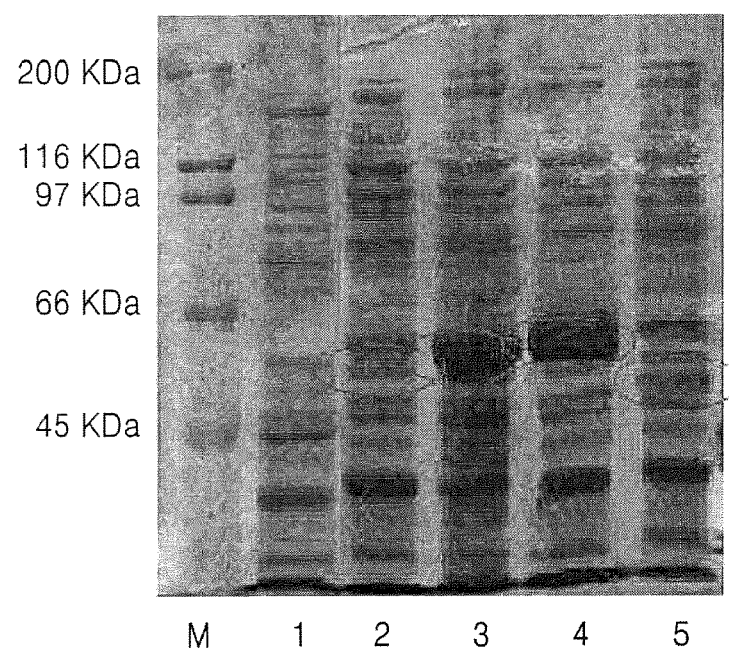
FIG. 7 is a SDS-PAGE image for crude extracts obtained from *E. coli* BL21 (DE3) strains respectively transformed with pT7-7carB, pT7-7carC, pT7-7carD, and pT7-7carE (M: marker, lane 1: negative control, lane 2: TMLH (52 KDa), lane 3: SHMT (53 KDa), lane 4: TMABADH (55 KDa), and lane 5: BBH (49 KDa))

The activity of TMLH expressed in the pT7-7carB-transformed *E. coli* BL21 (DE3) was investigated. First, the transformed *E. coli* culture was centrifuged at 4,000×g for 15 minutes and cell pellets were collected. The cell pellets were treated with 1 ml of a lysis buffer (140 mM NaCl, 200 g/l glycerol, and 1 mM DTT in 10 mM sodium phosphate buffer (pH 7.4)) and resuspended. The cell suspension was placed in an ice bath and ultrasonically treated using an ultrasonic homogenizer (×5, 10 seconds for each) to disrupt the cells. The cell lysate was centrifuged at 4° C. and 10,000 g for 20 to 30 minutes. The cell debris was removed and the supernatant was recovered to obtain a cell crude extract. 8% SDS-PAGE for a sample from the cell crude extract was performed (see FIG. 7). The SDS-PAGE results revealed the presence of an about 52 KDa band corresponding to TMLH.

(3) Amplification and Cloning of SHMT-Encoding Polynucleotide (carC Gene) and Detection of SHMT Production (a) Amplification and Cloning of SHMT-Encoding Polynucleotide (carC)

PCR was performed using the cDNA library pool-containing λ phages of (1) as template and oligonucleotides set forth in SEQ ID NOS: 3 and 4 as primers. The PCR products were subjected to agarose gel electrophoresis. As a result, desired PCR products of about 1.4 kb were identified. The primers of SEQ ID NOS: 3 and 4 included putative sequences encoding the start codon and the stop codon of *Neurospora crassa*-derived SHMT. The *Neurospora crassa*-derived SHMT was deduced by homology search between publicly available human- and rat-derived SHMT amino acid sequences and the amino acid sequences of total proteins expressed from *Neurospora crassa* genome, and the primers of SEQ ID NOS: 3 and 4 were designed based on the putative *Neurospora crassa*-derived SHMT.

Figure 3:
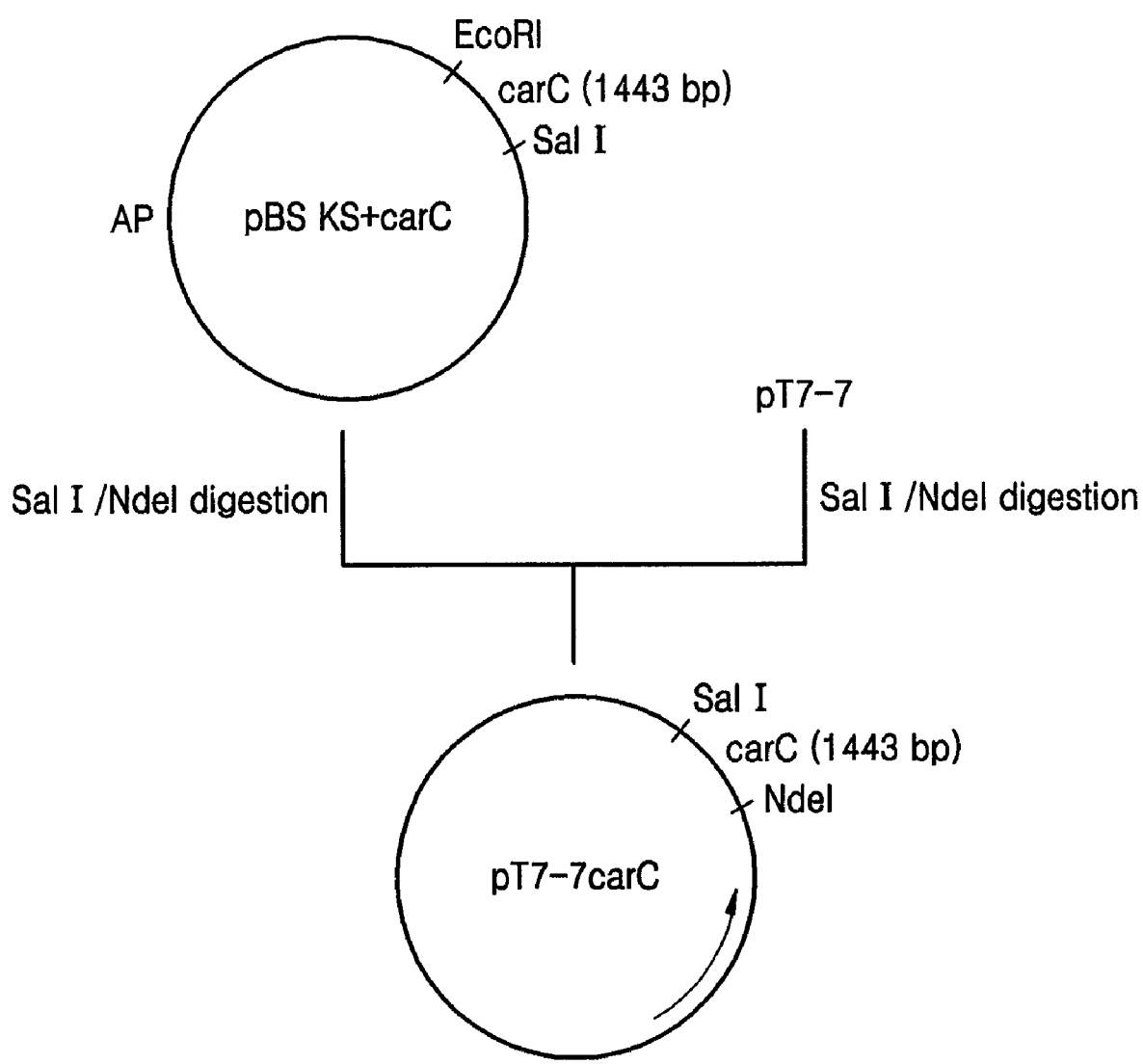
FIG. 3 is a diagram showing the construction of pT7-7carC.

The PCR products were digested with EcoRI and SalI, and ligated into pBS KS+ (Stratagene Inc.) which had been treated with the same restriction enzymes. pBS KS+carC obtained by inserting the PCR products into pBS KS+ was transformed into *E. coli* DH5α. The transformed *E. coli* DH5α was cultured at 37° C. for 8 hours. pBS KS+carC was separated from the transformed *E. coli* DH5α and treated with EcoRI and SalI to determine whether the PCR products were appropriately inserted into *E. coli* DH5α. Then, the separated pBS KS+carC was treated with NdeI and SalI and subjected to agarose gel electrophoresis to obtain NdeI-SalI fragments. The NdeI-SalI fragments were ligated into expression vectors pT7-7 which had been treated with the same restriction enzymes to obtain pT7-7carC (see FIG. 3). The pT7-7carC was transformed into *E. coli* BL21 (DE3).

(b) Detection of SHMT Production

The pT7-7carC-transformed *E. coli* BL21(DE3) was cultured at 37° C. in a 250 ml-baffled flask filled with 50 ml of an ampicillin (100 µg/ml)-supplemented LB medium until OD600 was 0.6. 1 mM of IPTG was added and the resultant cells were further cultured for four hours. pT7-7carC was separated from the cell culture and treated with NdeI and SalI, and the resultant restriction fragments were separated using agarose gel electrophoresis. The electrophoretic results are shown in FIG. 6. As shown in FIG. 6, a band corresponding to the NdeI-SalI fragment was observed (lane 3). The nucleotide sequence analysis of the carC in pT7-7carC revealed that the nucleotide sequence of the carB in pT7-7carB was the same as that found in the *Neurospora crassa* genome database of the NCBI (SEQ ID NO: [[18]]14).

The activity of SHMT expressed in the pT7-7carC-transformed *E. coli* BL21 (DE3) was investigated. First, the transformed *E. coli* culture was centrifuged at 4,000×g for 15 minutes and cell pellets were collected. The cell pellets were treated with 1 ml of a lysis buffer (140 mM NaCl, 200 g/l glycerol, and 1 mM DTT in 10 mM sodium phosphate buffer (pH 7.4)) and resuspended. The cell suspension was placed in an ice bath and ultrasonically treated using an ultrasonic homogenizer (×5, 10 seconds for each) to disrupt the cells. The cell lysate was centrifuged at 4° C. and 10,000 g for 20 to 30 minutes. The cell debris was removed and the supernatant was recovered to obtain a cell crude extract. 8% SDS-PAGE for a sample from the cell crude extract was performed (see FIG. 7). The SDS-PAGE results revealed the presence of an about 53 KDa band corresponding to SHMT.

(4) Amplification and Cloning of TMABADH-Encoding Polynucleotide (carD) and Detection of TMABADH Production (a) Amplification and Cloning of TMABADH-Encoding Polynucleotide (carD)

PCR was performed using the cDNA library pool-containing λ phages of (1) as template and oligonucleotides set forth in SEQ ID NOS: 5 and 6 as primers. The PCR products were subjected to agarose gel electrophoresis. As a result, desired PCR products of about 1.5 kb were identified. The primers of SEQ ID NOS: 5 and 6 included putative sequences encoding the start codon and the stop codon of *Neurospora crassa*-derived TMABADH. The *Neurospora crassa*-derived TMABADH was deduced by homology search between publicly available human- and rat-derived TMABADH amino acid sequences and the amino acid sequences of total proteins expressed from *Neurospora crassa* genome, and the primers of SEQ ID NOS: 5 and 6 were designed based on the putative *Neurospora crassa*-derived TMABADH.

Figure 4:
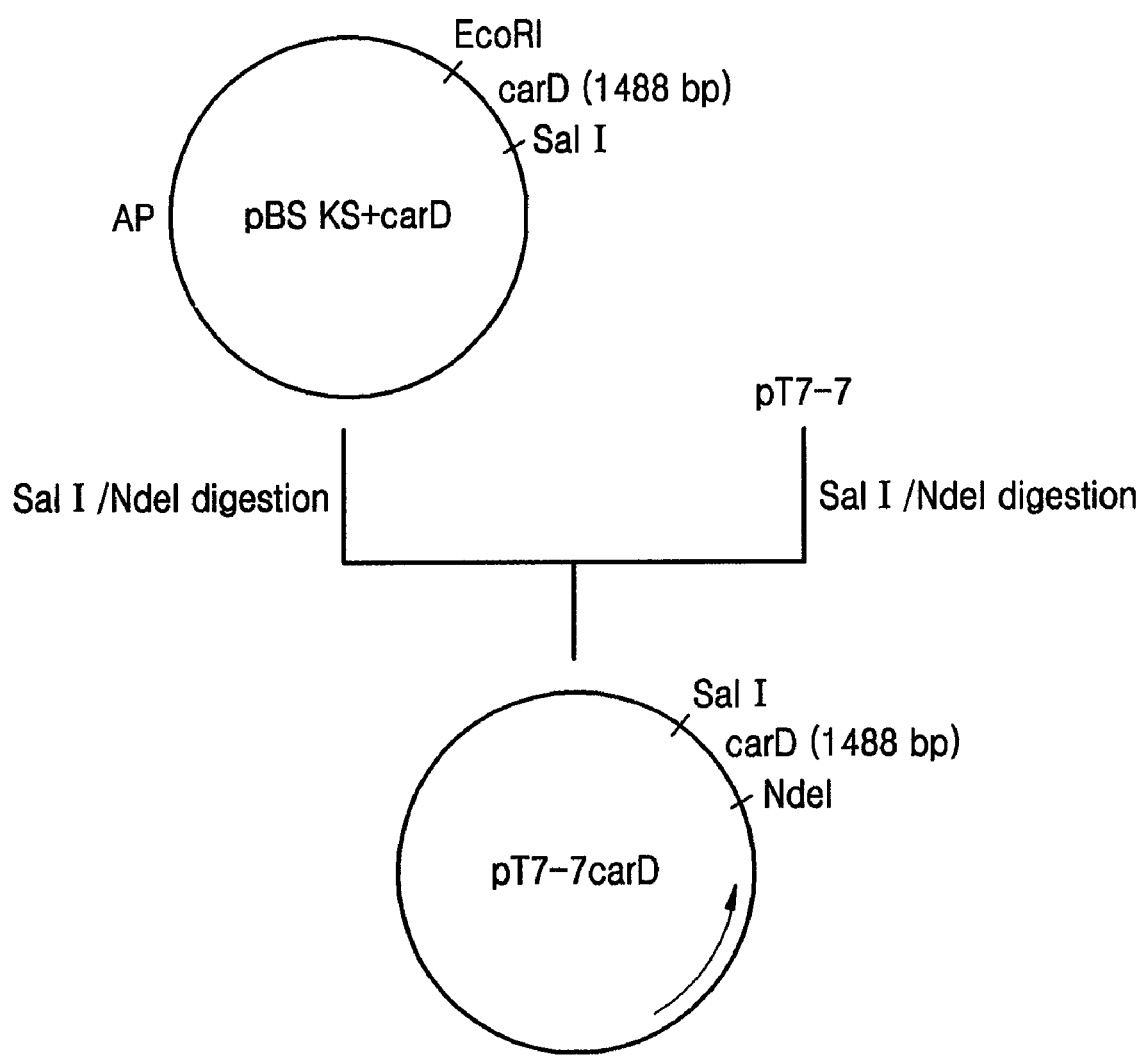
FIG. 4 is a diagram showing the construction of pT7-7carD.

The PCR products were digested with EcoRI and SalI, and ligated into pBS KS+ (Stratagene Inc.) which had been treated with the same restriction enzymes. pBS KS+carD obtained by inserting the PCR products into pBS KS+ was transformed into *E. coli* DH5α. The transformed *E. coli* DH5α was cultured at 37° C. for 8 hours. pBS KS+carD was separated from the transformed *E. coli* DH5α and treated with EcoRI and SalI to determine whether the PCR products were appropriately inserted into *E. coli* DH5α. Then, the separated pBS KS+carD was treated with NdeI and SalI and subjected to agarose gel electrophoresis to obtain NdeI-SalI fragments. The NdeI-SalI fragments were ligated into expression vectors pT7-7 which had been treated with the same restriction enzymes to obtain pT7-7carD (see FIG. 4). The pT7-7carD was transformed into *E. coli* BL21 (DE3).

(b) Detection of TMABADH Production

The pT7-7carD-transformed *E. coli* BL21(DE3) was cultured at 37° C. in a 250 ml-baffled flask filled with 50 ml of an ampicillin (100 μg/ml)-supplemented LB medium until OD600 was 0.6. 1 mM of IPTG was added and the resultant cells were further cultured for four hours. pT7-7carD was separated from the cell culture and treated with NdeI and SalI, and the resultant restriction fragments were separated using agarose gel electrophoresis. The electrophoretic results are shown in FIG. 6. As shown in FIG. 6, a band corresponding to the NdeI-SalI fragment was observed (lane 4). The nucleotide sequence analysis of the carD in pT7-7carD revealed that the nucleotide sequence of the carD in pT7-7carD was the same as that found in the *Neurospora crassa* genome database of the NCBI (SEQ ID NO: [[19]]15).

The activity of TMABADH expressed in the pT7-7carD-transformed *E. coli* BL21 (DE3) was investigated. First, the transformed *E. coli* culture was centrifuged at 4,000×g for 15 minutes and cell pellets were collected. The cell pellets were treated with 1 ml of a lysis buffer (140 mM NaCl, 200 g/l glycerol, and 1 mM DTT in 10 mM sodium phosphate buffer (pH 7.4)) and resuspended. The cell suspension was placed in an ice bath and ultrasonically treated using an ultrasonic homogenizer (×5, 10 seconds for each) to disrupt the cells. The cell lysate was centrifuged at 4° C. and 10,000 g for 20 to 30 minutes. The cell debris was removed and the supernatant was recovered to obtain a cell crude extract. 8% SDS-PAGE for a sample from the cell crude extract was performed (see FIG. 7). The SDS-PAGE results revealed the presence of an about 55 KDa band corresponding to TMABADH.

(5) Amplification and Cloning of BBH-Encoding Polynucleotide (carE) and Detection of BBH Production (a) Amplification and Cloning of BBH-Encoding Polynucleotide (carE)

PCR was performed using the cDNA library pool-containing λ phages of (1) as template and oligonucleotides set forth in SEQ ID NOS: 7 and 8 as primers. The PCR products were subjected to agarose gel electrophoresis. As a result, desired PCR products of about 1.3 kb were identified. The primers of SEQ ID NOS: 7 and 8 included putative sequences encoding the start codon and the stop codon of *Neurospora crassa*-derived BBH. The *Neurospora crassa*-derived BBH was deduced by homology search between publicly available human- and rat-derived BBH amino acid sequences and the amino acid sequences of total proteins expressed from *Neurospora crassa* genome, and the primers of SEQ ID NOS: 7 and 8 were designed based on the putative *Neurospora crassa*-derived BBH.

Figure 5:
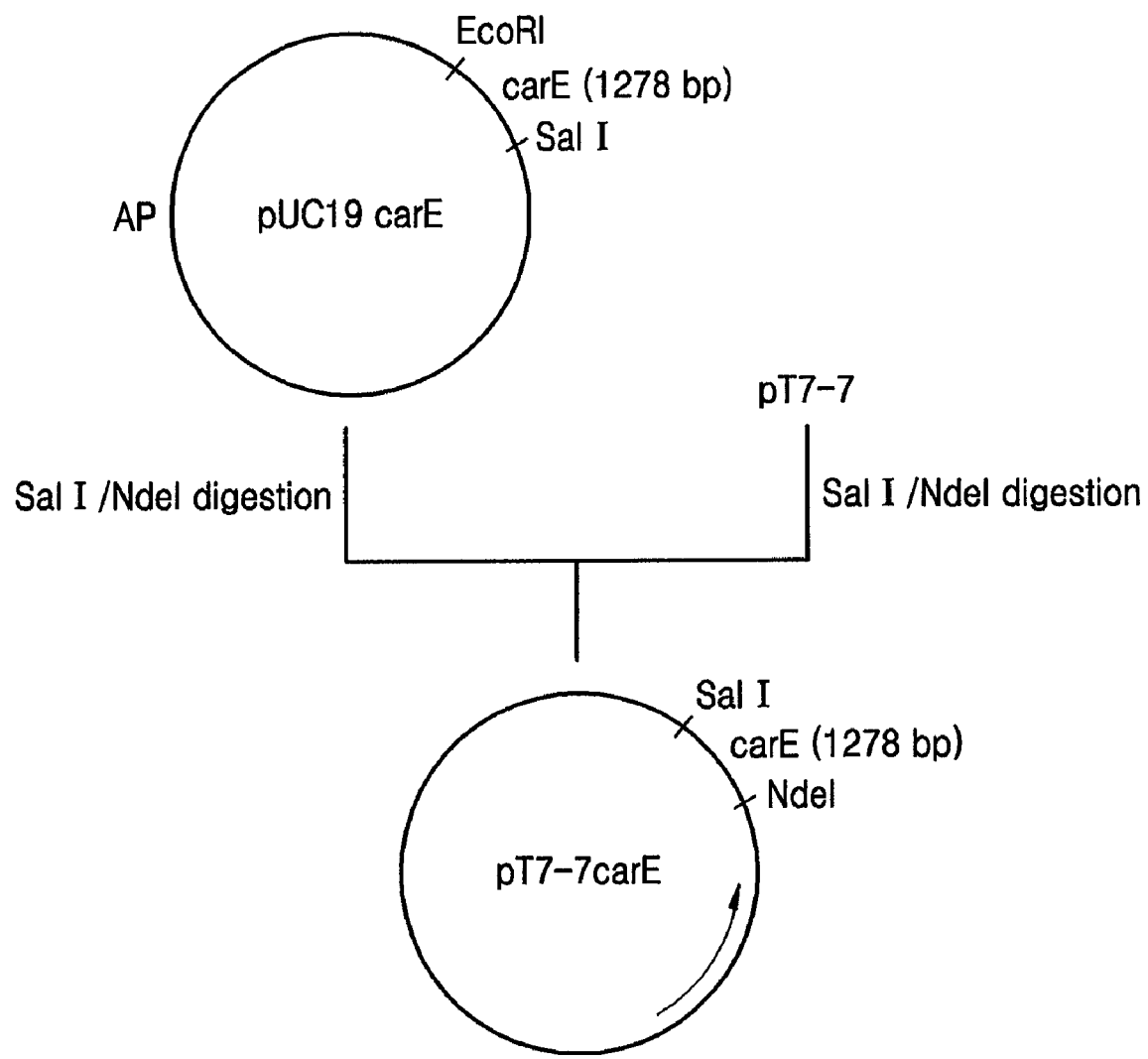
FIG. 5 is a diagram showing the construction of pT7-7carE.

The PCR products were digested with EcoRI and SalI, and ligated into pUC19 which had been treated with the same restriction enzymes. pUC19carE obtained by inserting the PCR products into pUC19 was transformed into *E. coli* DH5α. The transformed *E. coli* DH5α was cultured in an ampicillin (100 μg/Ml)-supplemented LB medium at 37° C. for 8 hours. pUC19carE was separated from the transformed *E. coli* DH5α and treated with EcoRI and SalI to determine whether the PCR products were appropriately inserted into *E. coli* DH5α. Then, the separated pUC19carE was treated with NdeI and SalI and subjected to agarose gel electrophoresis to obtain NdeI-SalI fragments. The NdeI-SalI fragments were ligated into expression vectors pT7-7 which had been treated with the same restriction enzymes to obtain pT7-7carE (see FIG. 5). The pT7-7carE was transformed into *E. coli* BL21 (DE3).

The pT7-7carE-transformed *E. coli* BL21(DE3) was cultured at 37° C. in a 250 ml-baffled flask filled with 50 ml of an ampicillin (100 μg/ml)-supplemented LB medium until OD600 was 0.6. 1 mM of IPTG was added and the resultant cells were further cultured for four hours. pT7-7carE was separated from the cell culture and treated with NdeI and SalI, and the resultant restriction fragments were separated using agarose gel electrophoresis. The electrophoretic results are shown in FIG. 6. As shown in FIG. 6, a band corresponding to the NdeI-SalI fragment was observed. The nucleotide sequence analysis of the carE (1,278 bp) in pT7-7carE revealed that the nucleotide sequence of the carE in pT7-7carE was the same as that found in the *Neurospora crassa* genome database of the NCBI (SEQ ID NO: 16).

(b) Detection of BBH Production

The activity of BBH expressed in the pT7-7carE-transformed *E. coli* BL21 (DE3) was investigated. First, the transformed *E. coli* culture was centrifuged at 4,000×g for 15 minutes and cell pellets were collected. The cell pellets were treated with 1 ml of a lysis buffer (140 mM NaCl, 200 g/l glycerol, and 1 mM DTT in 10 mM sodium phosphate buffer (pH 7.4)) and resuspended. The cell suspension was placed in an ice bath and ultrasonically treated using an ultrasonic homogenizer (×5, 10 seconds for each) to disrupt the cells. The cell lysate was centrifuged at 4° C. and 10,000 g for 20 to 30 minutes. The cell debris was removed and the supernatant was recovered to obtain a cell crude extract. 8% SDS-PAGE for a sample from the cell crude extract was performed (see FIG. 7). The SDS-PAGE results revealed the presence of an about 49 KDa band corresponding to BBH.

Example 2

Construction of Host Cells Containing carB, carC, carD, and carE

In this Example, the carB and carE genes were amplified from the *Neurospora crassa*-derived cDNA library prepared in Example 1, and pT7-7BE containing both the genes was constructed. Also, the carC and carD genes were amplified from the Neurospora crassa-derived cDNA library prepared in Example 1, and pACYC184CD containing both the genes was constructed. The pT7-7BE and pACYC184CD thus constructed were introduced into *E. coli* cells to obtain transformed cells containing all the carB, carC, carD and carE genes. The transformed cells were designated as *E. coli* DH5α CJ2004, and deposited in the international depository Korean Culture Center of Microorganisms (KCCM) on Jan. 27, 2004 (accession number: KCCM-10581).

(1) Construction of pT7-7BE Containing Both the carB and carE Genes

Figure 8:
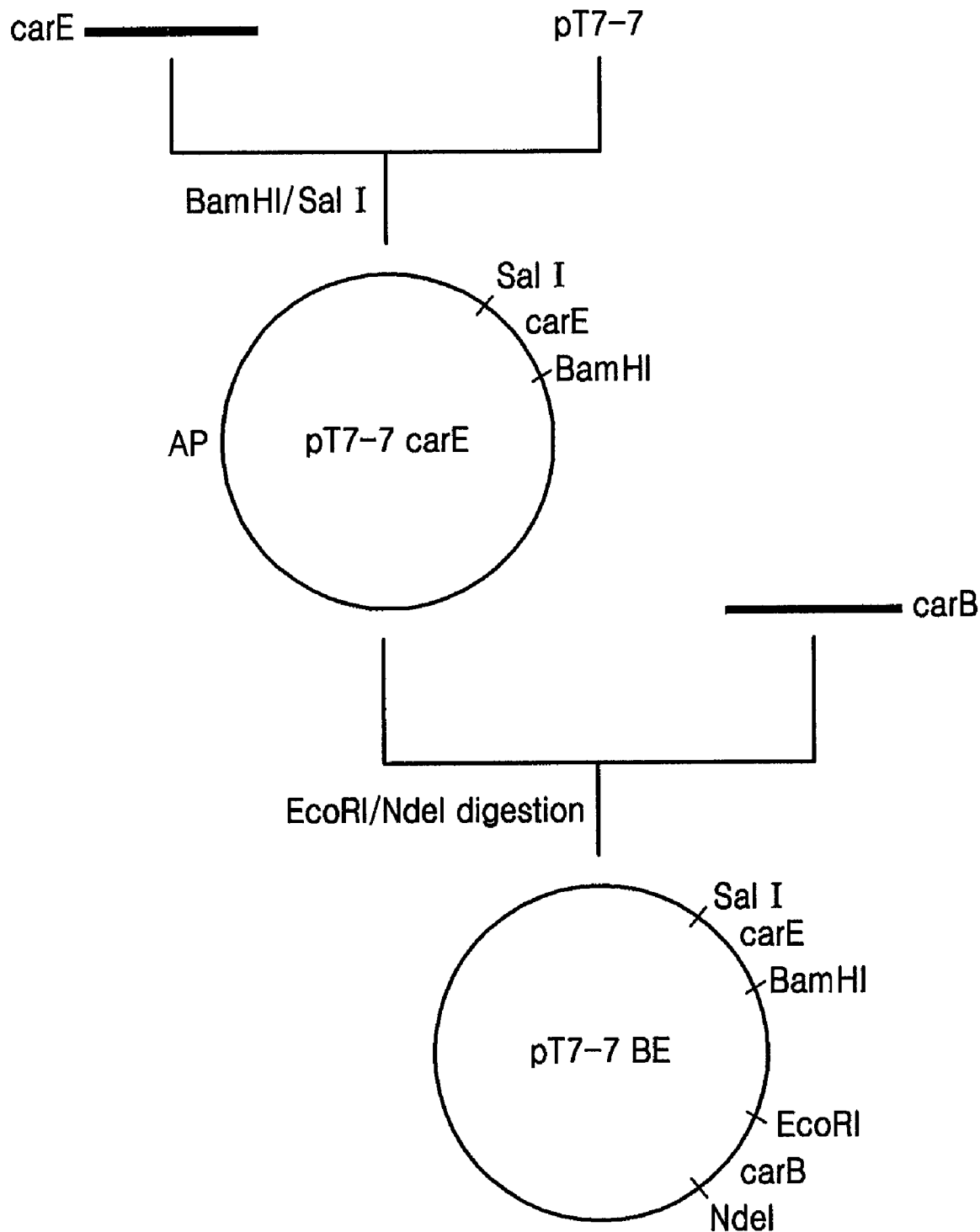
FIG. 8 is a diagram showing the construction of pT7-7BE.

First, the carB gene was amplified using the Neurospora crassa-derived cDNA library as a template and oligonucleotides of SEQ ID NOS: 1 and 2 as primers. Then, the carE containing the region from T7 promoter to the stop codon was amplified using the Neurospora crassa-derived cDNA library as a template and oligonucleotides of SEQ ID NOS: 7 and 8 as primers. The carB and carE amplification products were introduced into pT7-7. For this, first, the carE amplification product was treated with BamHI and SalI to obtain a BamHI-SalI fragment. The BamHI-SalI fragment was ligated into pT7-7 which had been treated with the same restriction enzymes, to obtain pT7-7carE. Then, the carB amplification product was treated with NdeI and EcoRI to obtain an NdeI-EcoRI fragment. The NdeI-EcoRI fragment was ligated into pT7-7carE which had been treated with the same restriction enzymes to obtain pT7-7BE (see FIG. 8).

(2) Construction of pACYC184CD Containing Both carC and carD Genes

Figure 9:
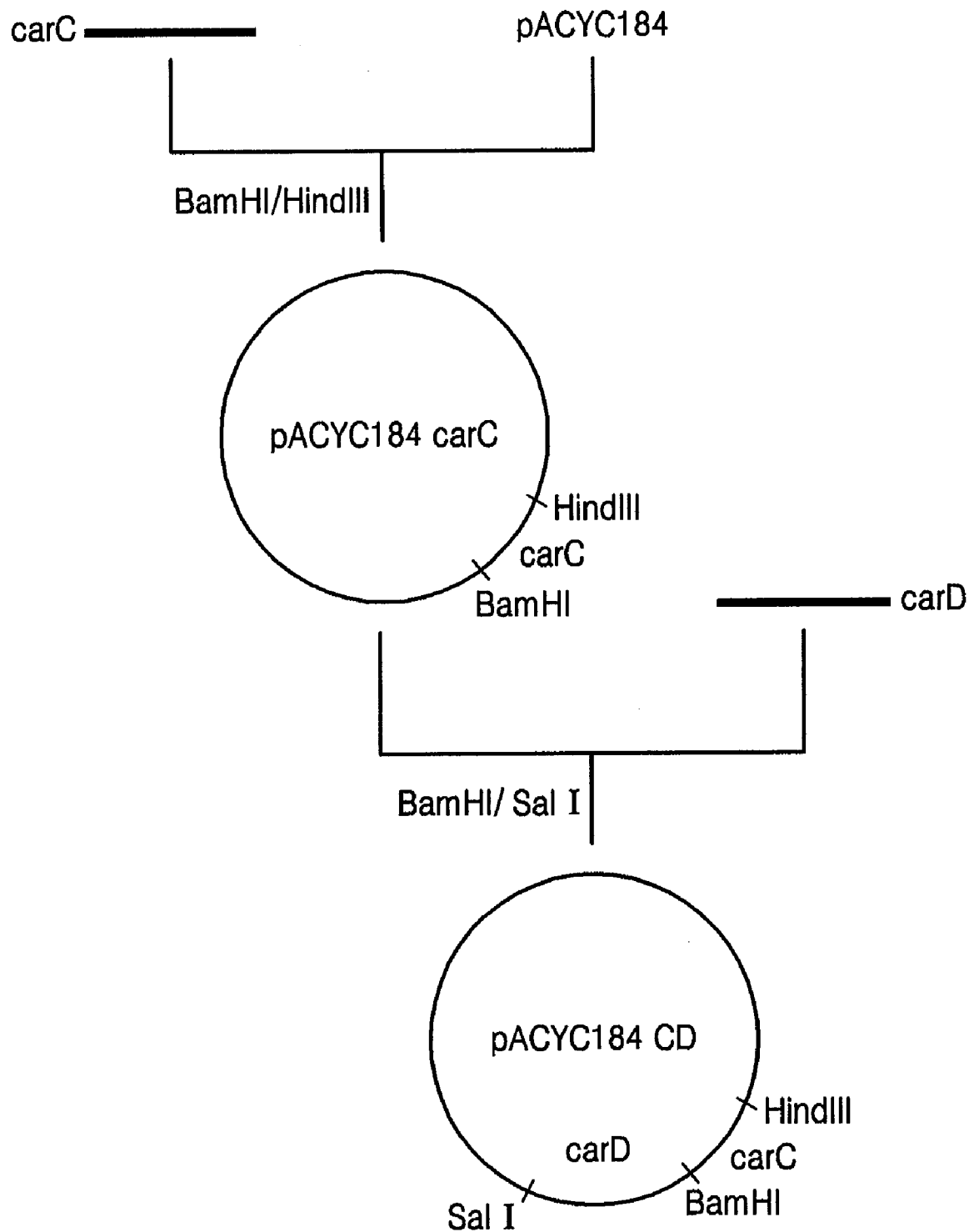
FIG. 9 is a diagram showing the construction of pACYC184CD.

First, the carC gene containing the region from T7 promoter to the stop codon was amplified using the Neurospora crassa-derived cDNA library as a template and oligonucleotides of SEQ ID NOS: 3 and 4 as primers. Then, the carD gene containing the region from T7 promoter to the stop codon was amplified using the Neurospora crassa-derived cDNA library as a template and oligonucleotides of SEQ ID NOS: 5 and 6 as primers. The carC and carD amplification products were introduced into pACYC184. For this, first, the carC amplification product was treated with BamHI and HIndIII to obtain a BamHI-HindIII fragment. The BamHI-HindIII fragment was ligated into pACYC184 which had been treated with the same restriction enzymes, to obtain pACYC184carC. Then, the carD amplification product was treated with BamHI and SalI to obtain a BamHI-SalI fragment. The BamHI-SalI fragment was ligated into pACYC184carC which had been treated with the same restriction enzymes to obtain pACYC184CD (see FIG. 9).

Example 3

Production of L-Carnitine Using Strains Containing Polynucleotides Encoding TMLH, SHMT, TMABADH and BBH In this Example, *E. coli* BL21 (DE3) strains respectively transformed with pT7-7carB, pT7-7carC, pT7-7carD, and pT7-7carE constructed in Example 1 were mixedly cultured in a trimethyllysine-containing medium and then the production of L-carnitine was measured. In addition, *E. coli* BL21 (DE3) strains co-transformed with pT7-7BE and pACYC184CD constructed in Example 2 were cultured and then the production of L-carnitine was measured.

(1) Mixed Culture of *E. coli* BL21 (DE3) Strains Respectively Transformed with pT7-7carB, pT7-7carC, pT7-7carD, and pT7-7carE First, the *E. coli* BL21 (DE3) strains respectively transformed with pT7-7carB, pT7-7carC, pT7-7carD, and pT7-7carE were plated onto ampicillin (100 µg/ml)-supplemented LB solid media and cultured. Cell colonies of each culture were cultured in a flask containing 20 ml of an ampicillin (100 µg/ml)-supplemented LB medium at 37° C. for 12 hours until OD600 was 1.0. Equal amounts (0.1 ml for each) of the cell cultures were added to a 250 ml-baffled flask containing 20 ml of a 2 mM trimethyllysine-containing, ampicillin (100 µg/ml)-supplemented LB medium and cultured at 37° C. until OD600 was 0.6. In the case of using IPTG, after OD600 reached 0.6, 1 mM of IPTG was added and the resultant cells were further cultured for four hours. A trimethyllysine-free LB medium was used as a control. The addition of IPTG and the cell culture were performed in the same manner as above.

After the culture, the content of L-carnitine in the cell culture was measured. 500 µl of the culture supernatant was harvested and mixed with 500 µl of 1.2 M perchloric acid. The mixed solution was incubated at room temperature for 10 minutes, and then centrifuged for 5 minutes. 600 µl of the resultant supernatant was mixed with 320 µl of 0.7 M $K_3PO_4$. The mixed solution was placed in an ice bath for 20 minutes and centrifuged for five minutes. 750 µl of the resultant supernatant was harvested and mixed with 250 µl of sterilized distilled water to obtain a diluted solution. 100 µl of DNTB/$H_2O_2$ was added to the diluted solution and the resultant solution was incubated for 10 minutes. 50 µl of a catalase solution was added, and the resultant solution was incubated at room temperature for 30 minutes and centrifuged to thereby harvest 1 ml of the resultant supernatant. 50 µl of acetyl CoA was added to the supernatant and the resultant solution was incubated at room temperature for five minutes. 2.26 µl of carnitine acetyltransferase was added and the resultant solution was incubated at room temperature for 10 minutes. Absorbance (405 nm) of the final solution was measured to calculate the content of L-carnitine. The results are presented in Table 1 below.

TABLE 1

| Production of L-carnitine by mixed culture | |
|---|---|
| Culture condition | Concentration (µg/Ml) |
| LB medium (IPTG induction) | 0 |
| LB medium containing 2 mM trimethyllysine (no IPTG induction) | 0.16 |
| LB medium containing 2 mM trimethyllysine (IPTG induction) | 0.97 |

As shown in Table 1, the mixed culture of the strains respectively containing a TMLH-encoding polynucleotide, a SHMT-encoding polynucleotide, a TMABADH-encoding polynucleotide, and a BBH-encoding polynucleotide in a trimethyllysine-containing medium enables production of L-carnitine in high yield.

(2) Production of L-Carnitine from *E. coli* BL21 (DE3) Culture Co-Transformed with pT7-7BE and pACYC184CD Constructed in Example 2

First, the *E. coli* BL21 (DE3) cultures respectively transformed with pT7-7BE and pACYC184CD were plated onto ampicillin (100 μg/ml)—and chloramphenicol (50 μg/ml)—supplemented LB solid media and cultured. Cell colonies of each culture were cultured in a flask containing 20 ml of an ampicillin (100 μg/ml)—and chloramphenicol (50 μg/ml)—supplemented LB medium at 37° C. for 12 hours until OD600 was 1.0. The equal amounts (0.1 ml for each) of the cell cultures were added to a 250 ml-baffled flask containing 20 ml of a 2 mM trimethyllysine-containing LB medium and cultured at 37° C. until OD600 was 0.6. In the case of using IPTG, after OD600 reached 0.6, 1 mM of IPTG was added and the resultant cells were further cultured for four hours. A trimethyllysine-free LB medium was used as a control. The addition of IPTG and the cell culture were performed in the same manner as above.

After the culture, the content of L-carnitine in the cell culture was measured in the same manner as in (1). The results are presented in Table 2 below.

TABLE 2

Production of L-carnitine by single culture

| Culture condition | Concentration (μg/Ml) |
|---|---|
| LB medium (IPTG induction) | 0 |
| LB medium containing 2 mM trimethyllysine (no IPTG induction) | 0.65 |
| LB medium containing 2 mM trimethyllysine (IPTG induction) | 1.12 |

As shown in Table 2, the culture of strains simultaneously containing polynucleotides encoding TMLH, SHMT, TMABADH and BBH in a trimethyllysine-containing medium enables production of L-carnitine in high yield. In comparison between the results presented in Tables 1 and 2, it can be seen that the L-carnitine yield by single culture is higher than that by mixed culture.

A microorganism belonging to the family Enterobacteriaceae according to the present invention has good L-carnitine productivity and thus can be effectively used in fermentative production of L-carnitine.

According to a process for producing L-carnitine of the present invention, L-carnitine can be produced in high yield using the microorganism.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microorganism belonging to the family Enterobacteriaceae transformed with nucleic acids comprising:
   a polynucleotide of *Neurospora crassa*, which encodes the amino acid sequence of SEQ ID NO: 9 having N-trimethyllysine hydroxylase activity;
   a polynucleotide of *Neurospora crassa*, which encodes the amino acid sequence of SEQ ID NO: 10 having 3-hydroxy-6-N-trimethyllysine aldolase activity;
   a polynucleotide of *Neurospora crassa*, which encodes the amino acid sequence of SEQ ID NO: 11 having γ-trimethylaminoaldehyde dehydrogenase activity; and
   a polynucleotide of *Neurospora crassa*, which encodes the amino acid sequence of SEQ ID NO: 12 having γ-butyrobetaine hydroxylase activity.

2. The microorganism of claim 1, which is *Escherichia coli*.

3. The microorganism of claim 1, which is *Escherichia coli* KCCM-10581.

4. A process for producing L-carnitine, which comprises culturing the microorganism of claim 1 in the presence of a substrate selected from the group consisting of ε-N-trimethyllysine, β-hydroxy-N-trimethyllysine, γ-N-trimethylaminobutyraldehyde, γ-butyrobetaine, and a mixture thereof, to produce L-carnitine in the culture.

5. The process of claim 4, wherein the concentration of the substrate selected from the group consisting of ε-N-trimethyllysine, β-hydroxy-N-trimethyllysine, γ-N-trimethylaminobutyraldehyde, γ-butyrobetaine, and a mixture thereof ranges from 0.1 to 10% weight compared to the weight of the culture medium.

6. A process for producing L-carnitine, which comprises culturing the microorganism of claim 2 in the presence of a substrate selected from the group consisting of ε-N-trimethyllysine, β-hydroxy-N-trimethyllysine, γ-N-trimethylaminobutyraldehyde, γ-butyrobetaine, and a mixture thereof, to produce L-carnitine in the culture.

7. A process for producing L-carnitine, which comprises culturing the microorganism of claim 3 in the presence of a substrate selected from the group consisting of ε-N-trimethyllysine, β-hydroxy-N-trimethyllysine, γ-N-trimethylaminobutyraldehyde, γ-butyrobetaine, and a mixture thereof, to produce L-carnitine in the culture.

* * * * *

SEQUENCE LISTING

```
<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 1
atgaattcca tatgagaccg caagtggtag gg                                32

<210> SEQ ID NO 2
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 2
atgaattctc attttccgct ggtttctttc cg                                32

<210> SEQ ID NO 3
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 3
atgaattcca tatgtctacc tactccctct cc                                32

<210> SEQ ID NO 4
<211> LENGTH: 30
<212> TYPE: DNA
```

```
<213> ORGANISM: Artificial Sequence
<220> FEATURE:
<223> OTHER INFORMATION: oligonucleotide primer

<400> SEQUENCE: 4
attgtcgact tagagaccgg catcgtatct                                        30

<210> SEQ ID NO 5
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 5
atgaattcca tatggaagtc gagcttacgg cc                                     32

<210> SEQ ID NO 6
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 6
attgtcgact catgccgcca ggtttacatg gat                                    33

<210> SEQ ID NO 7
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 7
atgaattcca tatgatggcc acggcagcgg ttcag                                  35

<210> SEQ ID NO 8
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 8
attagtcgac tcaataccct cccccaccct g                                      31

<210> SEQ ID NO 9
<211> LENGTH: 471
<212> TYPE: PRT
<213> ORGANISM: Neurospora crassa

<400> SEQUENCE: 9
```

Met Arg Pro Gln Val Val Gly Ala Ile Leu Arg Ser Arg Ala Val
1               5                   10                  15

Ser Arg Gln Pro Leu Ser Arg Thr His Ile Phe Ala Ala Val Thr Val
                20                  25                  30

Ala Lys Ser Ser Ser Pro Ala Gln Asn Ser Arg Arg Thr Phe Ser Ser
            35                  40                  45

Ser Phe Arg Arg Leu Tyr Glu Pro Lys Ala Glu Ile Thr Ala Glu Gly
        50                  55                  60

Leu Glu Leu Ser Pro Pro Gln Ala Val Thr Gly Gly Lys Arg Thr Val
65                  70                  75                  80

Leu Pro Asn Phe Trp Leu Arg Asp Asn Cys Arg Cys Thr Lys Cys Val

```
                    85                  90                  95
Asn Gln Asp Thr Leu Gln Arg Asn Phe Asn Thr Phe Ala Ile Pro Ser
                100                 105                 110

Asp Ile His Pro Thr Lys Val Glu Ala Thr Lys Glu Asn Val Thr Val
            115                 120                 125

Gln Trp Ser Asp Asn His Thr Ser Thr Tyr Pro Trp Pro Phe Leu Ser
        130                 135                 140

Phe Tyr Leu Thr Ser Asn Ala Arg Gly His Glu Asn Asp Gln Ile Ser
145                 150                 155                 160

Leu Trp Gly Ser Glu Ala Gly Ser Arg Pro Pro Thr Val Pro Phe Pro
                165                 170                 175

Arg Val Met Ala Ser Asp Gln Gly Val Ala Asp Leu Thr Ala Met Ile
            180                 185                 190

Lys Glu Phe Gly Phe Cys Phe Val Lys Asp Thr Pro His Asp Asp Pro
        195                 200                 205

Asp Val Thr Arg Gln Leu Leu Glu Arg Ile Ala Phe Ile Arg Val Thr
    210                 215                 220

His Tyr Gly Gly Phe Tyr Asp Phe Thr Pro Asp Leu Ala Met Ala Asp
225                 230                 235                 240

Thr Ala Tyr Thr Asn Leu Ala Leu Pro Ala His Thr Asp Thr Thr Tyr
                245                 250                 255

Phe Thr Asp Pro Ala Gly Leu Gln Ala Phe His Leu Leu Glu His Lys
            260                 265                 270

Ala Ala Pro Ser Arg Pro Pro Pro Pro Pro Pro Pro Pro Pro Pro Pro
        275                 280                 285

Ser Glu Glu Lys Glu Ala Ala Gly Ser Ala Ala Gly Glu Ala Ala Ala
    290                 295                 300

Ala Ala Glu Gly Gly Lys Ser Leu Leu Val Asp Gly Phe Asn Ala Ala
305                 310                 315                 320

Arg Ile Leu Lys Glu Glu Asp Pro Arg Ala Tyr Glu Ile Leu Ser Ser
                325                 330                 335

Val Arg Leu Pro Trp His Ala Ser Gly Asn Glu Gly Ile Thr Ile Ala
            340                 345                 350

Pro Asp Lys Leu Tyr Pro Val Leu Glu Leu Asn Glu Asp Thr Gly Glu
        355                 360                 365

Leu His Arg Val Arg Trp Asn Asn Asp Asp Arg Gly Val Val Pro Phe
    370                 375                 380

Gly Glu Lys Tyr Ser Pro Ser Glu Trp Tyr Glu Ala Ala Arg Lys Trp
385                 390                 395                 400

Asp Gly Ile Leu Arg Arg Lys Ser Ser Glu Leu Trp Val Gln Leu Glu
                405                 410                 415

Pro Gly Lys Pro Leu Ile Phe Asp Asn Trp Arg Val Leu His Gly Arg
            420                 425                 430

Ser Ala Phe Ser Gly Ile Arg Arg Ile Cys Gly Gly Tyr Ile Asn Arg
        435                 440                 445

Asp Asp Phe Ile Ser Arg Trp Arg Asn Thr Asn Tyr Pro Arg Ser Glu
    450                 455                 460

Val Leu Pro Arg Val Thr Gly
465                 470

<210> SEQ ID NO 10
<211> LENGTH: 480
<212> TYPE: PRT
<213> ORGANISM: Neurospora crassa
```

```
<400> SEQUENCE: 10

Met Ser Thr Tyr Ser Leu Ser Glu Thr His Lys Ala Met Leu Glu His
1               5                   10                  15

Ser Leu Val Glu Ser Asp Pro Gln Val Ala Glu Ile Met Lys Lys Glu
            20                  25                  30

Val Gln Arg Gln Arg Glu Ser Ile Ile Leu Ile Ala Ser Glu Asn Val
        35                  40                  45

Thr Ser Arg Ala Val Phe Asp Ala Leu Gly Ser Pro Met Ser Asn Lys
    50                  55                  60

Tyr Ser Glu Gly Leu Pro Gly Ala Arg Tyr Tyr Gly Gly Asn Gln His
65                  70                  75                  80

Ile Asp Glu Ile Glu Val Leu Cys Gln Asn Arg Ala Leu Glu Ala Phe
                85                  90                  95

His Leu Asp Pro Lys Gln Trp Gly Val Asn Val Gln Cys Leu Ser Gly
            100                 105                 110

Ser Pro Ala Asn Leu Gln Val Tyr Gln Ala Ile Met Pro Val His Gly
        115                 120                 125

Arg Leu Met Gly Leu Asp Leu Pro His Gly Gly His Leu Ser His Gly
    130                 135                 140

Tyr Gln Thr Pro Gln Arg Lys Ile Ser Ala Val Ser Thr Tyr Phe Glu
145                 150                 155                 160

Thr Met Pro Tyr Arg Val Asn Ile Asp Thr Gly Leu Ile Asp Tyr Asp
                165                 170                 175

Thr Leu Glu Lys Asn Ala Gln Leu Phe Arg Pro Lys Val Leu Val Ala
            180                 185                 190

Gly Thr Ser Ala Tyr Cys Arg Leu Ile Asp Tyr Glu Arg Met Arg Lys
        195                 200                 205

Ile Ala Asp Ser Val Gly Ala Tyr Leu Val Val Asp Met Ala His Ile
    210                 215                 220

Ser Gly Leu Ile Ala Ser Glu Val Ile Pro Ser Pro Phe Leu Tyr Ala
225                 230                 235                 240

Asp Val Val Thr Thr Thr Thr His Lys Ser Leu Arg Gly Pro Arg Gly
                245                 250                 255

Ala Met Ile Phe Phe Arg Arg Gly Val Arg Ser Val Asp Ala Lys Thr
            260                 265                 270

Gly Lys Glu Thr Leu Tyr Asp Leu Glu Asp Lys Ile Asn Phe Ser Val
        275                 280                 285

Phe Pro Gly His Gln Gly Gly Pro His Asn His Thr Ile Thr Ala Leu
    290                 295                 300

Ala Val Ala Leu Lys Gln Ala Ala Ser Pro Glu Phe Lys Glu Tyr Gln
305                 310                 315                 320

Gln Lys Val Val Ala Asn Ala Lys Ala Leu Glu Lys Lys Leu Lys Glu
                325                 330                 335

Leu Gly Tyr Lys Leu Val Ser Asp Gly Thr Asp Ser His Met Val Leu
            340                 345                 350

Val Asp Leu Arg Pro Ile Gly Val Asp Gly Ala Arg Val Glu Phe Leu
        355                 360                 365

Leu Glu Gln Ile Asn Ile Thr Cys Asn Lys Asn Ala Val Pro Gly Asp
    370                 375                 380

Lys Ser Ala Leu Thr Pro Gly Gly Leu Arg Ile Gly Thr Pro Ala Met
385                 390                 395                 400

Thr Ser Arg Gly Phe Gly Glu Ala Asp Phe Glu Lys Val Ala Val Phe
                405                 410                 415
```

-continued

Val Asp Glu Ala Val Lys Leu Cys Lys Glu Ile Gln Ala Ser Leu Pro
            420                 425                 430

Lys Glu Ala Asn Lys Gln Lys Asp Phe Lys Ala Lys Ile Ala Thr Ser
        435                 440                 445

Asp Ile Pro Arg Ile Asn Glu Leu Lys Gln Glu Ile Ala Ala Trp Ser
450                 455                 460

Asn Thr Phe Pro Leu Pro Val Glu Gly Trp Arg Tyr Asp Ala Gly Leu
465                 470                 475                 480

<210> SEQ ID NO 11
<211> LENGTH: 495
<212> TYPE: PRT
<213> ORGANISM: Neurospora crassa

<400> SEQUENCE: 11

Met Glu Val Glu Leu Thr Ala Pro Asn Gly Lys Lys Trp Met Gln Pro
1               5                   10                  15

Leu Gly Leu Phe Ile Asn Asn Glu Phe Val Lys Ser Ala Asn Glu Gln
            20                  25                  30

Lys Leu Ile Ser Ile Asn Pro Thr Thr Glu Glu Ile Cys Ser Val
        35                  40                  45

Tyr Ala Ala Thr Ala Glu Asp Val Asp Ala Ala Val Ser Ala Ala Arg
50                  55                  60

Lys Ala Phe Arg His Glu Ser Trp Lys Ser Leu Ser Gly Thr Glu Arg
65                  70                  75                  80

Gly Ala Leu Met Arg Lys Leu Ala Asp Leu Val Ala Glu Asn Ala Glu
            85                  90                  95

Ile Leu Ala Thr Ile Glu Cys Leu Asp Asn Gly Lys Pro Tyr Gln Thr
            100                 105                 110

Ala Leu Asn Glu Asn Val Pro Glu Val Ile Asn Val Leu Arg Tyr Tyr
        115                 120                 125

Ala Gly Tyr Ala Asp Lys Asn Phe Gly Gln Val Ile Asp Val Gly Pro
130                 135                 140

Ala Lys Phe Ala Tyr Thr Val Lys Glu Pro Leu Gly Val Cys Gly Gln
145                 150                 155                 160

Ile Ile Pro Trp Asn Tyr Pro Leu Asp Met Ala Ala Trp Lys Leu Gly
            165                 170                 175

Pro Ala Leu Cys Cys Gly Asn Thr Val Val Lys Leu Ala Glu Gln
        180                 185                 190

Thr Pro Leu Ser Val Leu Tyr Leu Ala Lys Leu Ile Lys Glu Ala Gly
        195                 200                 205

Phe Pro Pro Gly Val Ile Asn Ile Ile Asn Gly His Gly Arg Glu Ala
210                 215                 220

Gly Ala Ala Leu Val Gln His Pro Gln Val Asp Lys Ile Ala Phe Thr
225                 230                 235                 240

Gly Ser Thr Thr Thr Gly Lys Glu Ile Met Lys Met Ala Ser Tyr Thr
            245                 250                 255

Met Lys Asn Ile Thr Leu Glu Thr Gly Gly Lys Ser Pro Leu Ile Val
        260                 265                 270

Phe Glu Asp Ala Asp Leu Glu Leu Ala Ala Thr Trp Ser His Ile Gly
        275                 280                 285

Ile Met Ser Asn Gln Gly Gln Ile Cys Thr Ala Thr Ser Arg Ile Leu
        290                 295                 300

Val His Glu Lys Ile Tyr Asp Glu Phe Val Glu Lys Phe Lys Ala Lys
305                 310                 315                 320

-continued

```
Val Gln Glu Val Ser Val Leu Gly Asp Pro Phe Glu Ser Thr Phe
                325                 330                 335

His Gly Pro Gln Val Thr Lys Ala Gln Tyr Glu Arg Val Leu Gly Tyr
            340                 345                 350

Ile Asn Val Gly Lys Glu Gly Ala Thr Val Met Met Gly Gly Glu
            355                 360                 365

Pro Ala Pro Gln Asn Gly Lys Gly Phe Phe Val Ala Pro Thr Val Phe
    370                 375                 380

Thr Asn Val Lys Pro Thr Met Lys Ile Phe Arg Glu Glu Ile Phe Gly
385                 390                 395                 400

Pro Cys Val Ala Ile Thr Thr Phe Lys Thr Glu Glu Ala Leu Thr
                405                 410                 415

Leu Ala Asn Asp Ser Met Tyr Gly Leu Gly Ala Ala Leu Phe Thr Lys
                420                 425                 430

Asp Leu Thr Arg Ala His Arg Val Ala Arg Glu Ile Glu Ala Gly Met
                435                 440                 445

Val Trp Val Asn Ser Ser Asn Asp Ser Asp Phe Arg Ile Pro Phe Gly
    450                 455                 460

Gly Val Lys Gln Ser Gly Ile Gly Arg Glu Leu Gly Glu Ala Gly Leu
465                 470                 475                 480

Ala Pro Tyr Cys Asn Val Lys Ser Ile His Val Asn Leu Ala Ala
                485                 490                 495

<210> SEQ ID NO 12
<211> LENGTH: 425
<212> TYPE: PRT
<213> ORGANISM: Neurospora crassa

<400> SEQUENCE: 12

Met Ala Thr Ala Ala Val Gln Val Ser Val Pro Ala Pro Val Gly Gln
1               5                   10                  15

Pro Asp Ile Gly Tyr Ala Pro Asp His Asp Lys Tyr Leu Ala Arg Val
            20                  25                  30

Lys Arg Arg Arg Glu Asn Glu Lys Leu Glu Ser Ser Leu Pro Pro Gly
        35                  40                  45

Phe Pro Arg Arg Leu Asp Ser Asp Leu Val Trp Asp Gly Asn Thr Leu
    50                  55                  60

Ala Glu Thr Tyr Asp Trp Thr Tyr Arg Leu Thr Glu Glu Ala Ile Asp
65                  70                  75                  80

Glu Ile Glu Ala Ala Leu Arg His Phe Lys Ser Leu Asn Lys Pro Leu
                85                  90                  95

Gly Tyr Ile Asn Gln Glu Thr Phe Pro Leu Pro Arg Leu His His Thr
            100                 105                 110

Leu Arg Ser Leu Ser His Glu Leu His His Gly His Phe Lys Val
        115                 120                 125

Leu Arg Gly Leu Pro Val Thr Ser His Thr Arg Glu Glu Asn Ile Ile
    130                 135                 140

Ile Tyr Ala Gly Val Ser Ser His Val Ala Pro Ile Arg Gly Arg Gln
145                 150                 155                 160

Asp Asn Gln His Asn Gly His Pro Ala Asp Val Val Leu Ala His Ile
                165                 170                 175

Lys Asp Leu Ser Thr Thr Val Ser Asp Val Ser Lys Ile Gly Ala Pro
            180                 185                 190

Ala Tyr Thr Thr Glu Lys Gln Val Phe His Thr Asp Ala Gly Asp Ile
        195                 200                 205
```

```
Val Ala Leu Phe Cys Leu Gly Glu Ala Ala Glu Gly Gln Ser Tyr
        210                 215                 220

Leu Ser Ser Ser Trp Lys Val Tyr Asn Glu Leu Ala Ala Thr Arg Pro
225                 230                 235                 240

Asp Leu Val Arg Thr Leu Ala Glu Pro Trp Val Ala Asp Glu Phe Gly
            245                 250                 255

Lys Glu Gly Arg Lys Phe Ser Val Arg Pro Leu Leu His Phe Gln Ser
        260                 265                 270

Thr Ala Ala Ala Ser Arg Glu Ala Lys Pro Glu Ser Glu Arg Leu
        275                 280                 285

Ile Ile Gln Tyr Ala Arg Arg Thr Phe Thr Gly Tyr Trp Gly Leu Pro
        290                 295                 300

Arg Ser Ala Asp Ile Pro Pro Ile Thr Glu Ala Gln Ala Glu Ala Leu
305                 310                 315                 320

Asp Ala Leu His Phe Thr Ala Glu Lys Tyr Ala Val Ala Leu Asp Phe
            325                 330                 335

Arg Gln Gly Asp Val Gln Phe Val Asn Asn Leu Ser Val Phe His Ser
        340                 345                 350

Arg Ala Gly Phe Arg Asp Glu Gly Glu Lys Gln Arg His Leu Val Arg
        355                 360                 365

Leu Trp Leu Arg Asp Pro Glu Asn Ala Trp Glu Thr Pro Glu Ala Leu
370                 375                 380

Lys Glu Arg Trp Glu Arg Val Tyr Gly Gly Val Ser Pro Gly Arg Glu
385                 390                 395                 400

Val Phe Pro Leu Glu Pro Gln Ile Arg Ser Ala Ser Lys Gly Glu Ser
            405                 410                 415

Val Gly Thr Gln Gly Gly Gly Gly Tyr
        420                 425

<210> SEQ ID NO 13
<211> LENGTH: 1407
<212> TYPE: DNA
<213> ORGANISM: Neurospora crassa

<400> SEQUENCE: 13
atgagaccgc aagtggtagg ggcaatcctc cgctctagag ctgttgtcag cagacaacct       60 cttcgagga cccatatctt tgctgccgtc actgttgcaa gtcctcatc acctgcccag       120 aactcgagaa gaacctttc atcctctttc cgacggttgt atgagccaaa ggcggagata       180
acagctgagg gacttgagtt gagccctcca caggctgtta cgggtggaaa gcggactgtt       240
ttacccaact tctggctacg tgacaactgc cggtgtacga aatgcgtgaa ccaagatact       300
ctccagagaa acttcaacac ttttgccatc ccctccgaca tccacccaac aaaggttgaa       360
gccaccaagg agaacgtcac cgtccaatgg tccgacaacc acacatccac ctaccctgg       420 cccttcctct ctttctacct cacctccaac gcgcgcgggc acgaaaacga ccagatctcc       480
ctctggggct ccgaagccgg ctcccgcccg ccaaccgtct ccttccctcg cgtgatggca       540
tcagaccagg gcgtcgccga cctaaccgcc atgatcaaag agttcggctt ctgttttcgtc       600 aaagacacac cccatgacga cccggacgtg acccgccagc ttctggagag aatcgccttt       660
atccgagtga cccattacgg cggcttttac gatttcacgc ccgacctcgc gatgccgac       720 acggcgtaca cgaacctggc gctgccggcg catacggata cgacgtactt cacggacccg       780
gcggggttgc aggcttttca cttgttggag cataaggccg ctcctctcg tcctcctcct       840 cctcctcctc ctcctcctcc tccttctgaa gaaaaagaag ctgcaggctc agcagcaggg       900
```

```
gaggcggcgg cggcagcaga agggggaaag tcgttgttgg tcgatgggtt caacgccgcg      960
aggattctga aggaggagga tccccgggct tatgagatct tgagcagcgt gagactgccg     1020
tggcatgcga gtggaaacga agggatcacg attgcgcccg ataagcttta tccggtgctg     1080
gaactgaatg aggataccgg ggaactgcat agggttaggt ggaataatga tgataggggt     1140
gtggtgccgt ttggggagaa gtacagcccg tcagagtggt atgaggcggc gaggaagtgg     1200
gatgggattt tgaggaggaa gagcagcgag ttgtgggtgc agttggagcc ggggaagccg     1260
ttgaggttct tcatggacgg agcgcgttct cgggtattag gaggatttgt ggagggtata     1320
tcaaccgcga tgacttcatc tctcggtgga ggaacacgaa ttacccaagg agcgaggttc     1380
ttccgagggt tactggttaa ggactga                                         1407

<210> SEQ ID NO 14
<211> LENGTH: 1443
<212> TYPE: DNA
<213> ORGANISM: Neurospora crassa

<400> SEQUENCE: 14
atgtctacct actccctctc cgagactcac aaggccatgc tcgagcatag cttggtcgag       60
tccgaccccc aggtcgccga gatcatgaag aaggaggttc agcgccagcg cgagtccatc      120
atcctcatcg cctccgagaa cgtcacctcg cgtgccgtct tcgatgccct cggctccccc      180
atgtccaaca agtactcgga gggtcttccc ggcgcccgct actatggtgg caaccagcac      240
atcgacgaga tcgaggttct ctgccagaac cgtgccttg aggccttcca cctcgacccc       300
aagcagtggg gtgtcaatgt tcagtgcttg tccggcagcc ctgccaacct ccaggtctac      360
caggccatca tgcccgtcca cggcagactc atgggtcttg acctccccca cggtggccat      420
ctttcccacg gttaccagac ccccagcgc aagatctctg ctgtctctac ctacttcgag       480
accatgccct accgcgtcaa cattgacact ggtctcatcg actacgatac cctcgagaag      540 aacgccagc tcttccgccc caaggtcctc gtcgccggta cctctgccta ctgccgtctg       600
attgactacg agcgcatgcg caagattgcc gactccgttg gcgcttacct tgtcgtcgat      660
atggctcaca tttccggcct cattgcctcc gaggttatcc cctcgccctt cctctacgcc      720
gatgtcgtca ccaccaccac tcacaagtct ctccgtggcc ctcgtggcgc atgatcttc       780 ttccgccgcg gtgccgctc cgttgacgcc aagaccggca aggagaccct ctacgacctt      840
gaggacaaga tcaacttctc cgtcttccct ggtcaccagg gtggccccca caaccacacc      900
atcaccgccc ttgccgttgc cctcaagcag gctgcctccc ccgagttcaa ggagtaccag      960
cagaaggtcg ttgccaacgc caaggctctc gagaagaagc tcaaggagct cggctacaag     1020
ctcgtctctg acggcactga ctctcacatg gtcctcgttg accttcgccc catcggcgtc     1080
gatggtgccc gtgttgagtt cctccttgag cagatcaaca ttacctgcaa caagaacgcc     1140
gttcccggcg acaagagcgc cctcaccccc ggcggtctcc gtattggtac ccccgctatg     1200
acctcccgtg gcttcggcga ggccgacttc gagaaggtcg ccgtcttcgt cgatgaggct     1260
gtcaagctct gcaaggagat ccaggcttcc ctccccaagg aggctaacaa gcagaaggac     1320
ttcaaggcca agatcgccac cagcgatatt ccccgcatca acgagctcaa gcaggagatt     1380
gccgcctgga gcaacacctt cccccctccc gttgagggct ggagatacga tgccggtctc     1440
taa                                                                  1443

<210> SEQ ID NO 15
<211> LENGTH: 1488
<212> TYPE: DNA
```

<213> ORGANISM: Neurospora crassa

<400> SEQUENCE: 15

| | | | | | |
|---|---|---|---|---|---|
| atggaagtcg | agcttacggc | ccccaacggc | aagaagtgga | tgcagccact | gggcttgttc | 60 |
| attaataacg | agtttgtcaa | aagtgccaat | gagcagaagt | tgatttccat | caacccaact | 120 |
| accgaagagg | agatctgctc | ggtatacgcc | gcaaccgccg | aggatgttga | cgccgcagta | 180 |
| tcagcagccc | gcaaggcctt | taggcacgaa | tcatggaagt | cgctatccgg | cactgagcgc | 240 |
| ggcgccctga | tgcgcaagct | ggccgaccta | gtggccgaga | atgccgaaat | cctagccacc | 300 |
| atcgagtgcc | tggacaacgg | caagccgtat | cagacagccc | ttaacgagaa | cgtgcccgaa | 360 |
| gtgatcaacg | tcctcaggta | ctatgccggc | tatgcggaca | agaactttgg | ccaagtgatt | 420 |
| gacgttggcc | ccgccaagtt | tgcctacacg | gtcaaggagc | tctcggcgt | atgtggccag | 480 |
| atcatcccct | ggaactaccc | gctagatatg | gccgcctgga | agctggggcc | agctctctgc | 540 |
| tgcggcaaca | ccgtggtcct | caagctggcc | gagcagactc | ccctgtccgt | gttgtacttg | 600 |
| gctaagctca | ttaaggaggc | cggcttccct | cccggtgtga | tcaatatcat | caacggacac | 660 |
| ggcagggaag | cgggtgccgc | acttgtgcaa | catcctcagg | tggacaagat | tgcctttacc | 720 |
| ggcagcacca | ctacgggcaa | ggagatcatg | aagatggctt | cctataccat | gaagaacatc | 780 |
| accctggaga | ctggcggcaa | gtcaccgttg | atcgtgtttg | aggatgccga | ccttgagctg | 840 |
| gcggcgacat | ggtcacacat | cggcatcatg | agcaaccagg | gccaaatctg | cacagccact | 900 |
| tcacgcattc | tcgtgcacga | aagatctac | gacgagtttg | tcgaaaaatt | caaggccaaa | 960 |
| gtccaggagg | tttcggtact | cggcgacccc | ttcgaggaga | gcacgttcca | cggacctcag | 1020 |
| gtcaccaaag | cgcagtatga | gcgtgttctg | ggctatatca | atgtcggaaa | ggaagagggt | 1080 |
| gccacggtga | tgatgggtgg | tgagccggct | ccgcagaacg | gtaaaggttt | ctttgtggcc | 1140 |
| ccgactgtct | tcacgaacgt | caagccgacc | atgaagatct | tcaggagga | gatctttggg | 1200 |
| ccctgcgtgg | ccattaccac | gttcaaaacg | gaggaggagg | cgttgacgct | ggccaacgac | 1260 |
| agcatgtatg | gcctgggagc | ggctctgttc | accaaggacc | taaccagggc | acacagagtg | 1320 |
| gcgcgggaga | tcgaggccgg | catggtctgg | gtcaacagca | gcaacgattc | agactttagg | 1380 |
| attccatttg | gaggcgtgaa | gcagtctggt | attgggaggg | agttgggaga | ggcaggtctg | 1440 |
| gcaccttatt | gcaacgtcaa | gagtatccat | gtaaacctgg | cggcatga | | 1488 |

<210> SEQ ID NO 16
<211> LENGTH: 1278
<212> TYPE: DNA
<213> ORGANISM: Neurospora crassa

<400> SEQUENCE: 16

| | | | | | |
|---|---|---|---|---|---|
| atggccacgg | cagcggttca | ggtttcagtc | ccagctccgg | ttggacaacc | agatatcggg | 60 |
| tacgctcctg | accacgacaa | gtacctcgca | agagtcaaaa | gacgacgaga | aaacgagaag | 120 |
| ctggagtcgt | ctcttccgcc | aggtttccct | cgaagactag | actcggacct | tgtgtgggac | 180 |
| ggcaacaccc | tcgccgagac | gtacgactgg | acctacagac | tgacagaaga | ggccattgat | 240 |
| gaaatcgagg | ccgcgcttcg | tcattttaag | agcctcaaca | agcccctagg | ctacatcaac | 300 |
| caagaaacct | tcccccttcc | ccgcctacac | cacactctcc | gctccctctc | ccacgagctc | 360 |
| caccacggcc | acggcttcaa | agtcctccgc | gggctccccg | tcacctccca | tacacgcgag | 420 |
| gaaaacatca | tcatctacgc | cggcgtctcc | tcgcatgtcg | ctcctatccg | cggccgccag | 480 |
| gacaaccagc | acaacggcca | cccagccgac | gtagtcctag | cacacatcaa | agacctgtcc | 540 |

-continued

```
acgactgttt ctgacgtgag caaaatcggt gcacccgcct acaccaccga gaaacaagtc       600
ttccacaccg acgcaggcga catcgtcgcc ctcttttgct tgggagaggc cgccgagggc       660
ggacagagtt acctgtccag cagctggaag gtgtacaacg agctggcagc cactcggccc       720
gatctggttc gcacgctggc ggagccgtgg gtggcggacg agtttggcaa ggaagggagg       780 aagtttctg tgcgaccgct tttgcatttt cagtctactg ctgctgctgc ttctagggaa       840
gcaaagcccg agtctgaacg gctcatcatc cagtacgccc gccgcacgtt tacgggtat       900 tggggattac cgaggtcggc ggatatcccg cccattacgg aggcgcaggc ggaggcgttg       960
gatgcgctgc actttacggc ggagaagtac gcggtggcgc tggatttcag gcaggggat      1020 gtccagtttg tgaataactt gagtgtgttc cattcgaggg cggggtttag agatgagggg      1080
gagaagcaga ggcatttggt taggttgtgg ttgagagatc cggagaatgc gtgggagacg      1140
cccgaggcgt tgaaggaacg gtgggaacgc gtgtatggcg gggtgagtcc ggagagggag      1200
gtgtttccgc ttgagccgca gattaggagc gcgagtaagg gggagagcgt ggggacgcag      1260
ggtgggggag ggtattga                                                   1278
```